Figure 1:
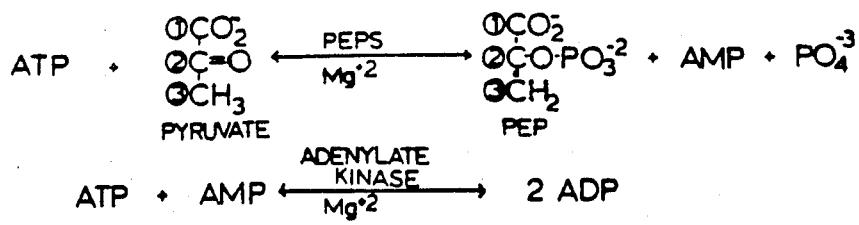
Figure 1:
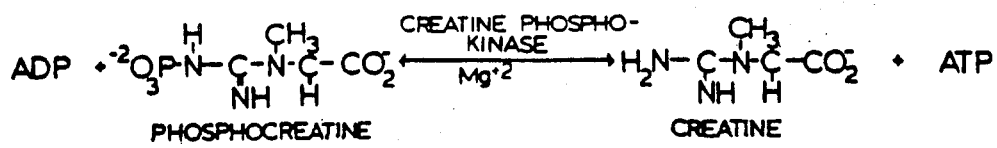
Figure 1:
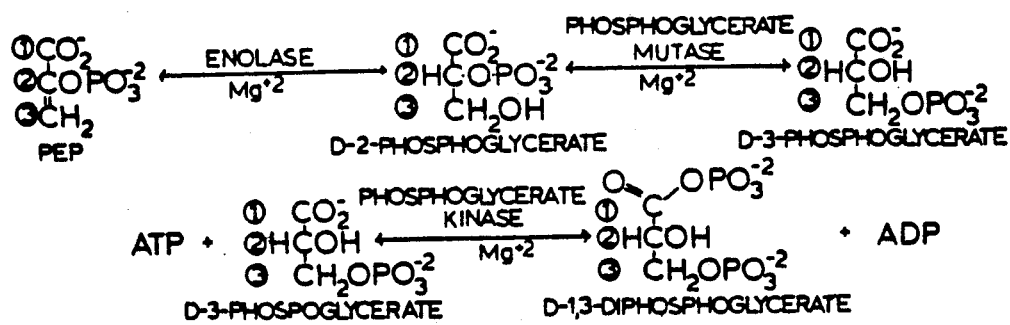
Figure 1:
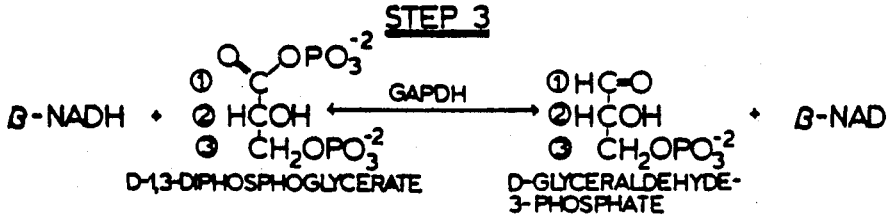
Figure 1:
Figure 1:
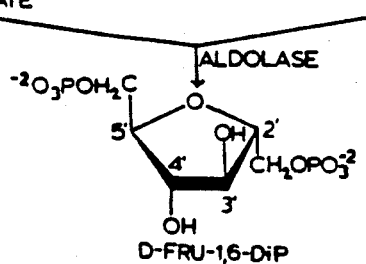

United States Patent [19]

Goux

[11] Patent Number: 4,656,133

[45] Date of Patent: Apr. 7, 1987

[54] METHOD FOR ENZYMATIC SYNTHESIS OF ISOTOPICALLY LABELED CARBOHYDRATES

[75] Inventor: Warren J. Goux, Richardson, Tex.

[73] Assignee: Board of Regents, University of Texas System, Austin, Tex.

[21] Appl. No.: 537,721

[22] Filed: Sep. 29, 1983

[51] Int. Cl.[4] .................. C12P 19/00; C12P 19/02; C12N 9/04; C12N 9/12

[52] U.S. Cl. .................................... 435/72; 435/105; 435/190; 435/194

[58] Field of Search ................. 435/72, 105, 190, 194

[56] References Cited

U.S. PATENT DOCUMENTS 4,209,589  6/1980  Johnson et al. ..................... 435/90
4,440,854  4/1984  Whitesides et al. ............. 435/105 X

OTHER PUBLICATIONS

Serianni, A. S. et al., "Carbon-13-Enriched Carbohydrates: Preparation of Triose, Tetrose and Pentose Phosphates", 18 Biochemistry 1192–1199 (1979).

Serianni, A. S. et al., "Carbon-13-Enriched Carbohydrates, Preparation of Aldonitriles and Their Reduction with a Palladium Catalyst", 72 Carbohydrate Res. 71–78 (1979).

Serianni, A. S. et al., "Carbon-13-Enriched Carbohydrates, Preparation of Erythrose, Threose, Glyceraldehyde and Glycoaldehyde with $^{13}$C-Enrichment in Various Carbon Atoms", 72 Carbohydrate Res. 79–91 (1979).

Rognstad, R. et al., "Enzymic Synthesis of Glucose-4-Tritium and Glucose-3-Tritium", 109 Archives of Biochemistry and Biophysics 372–375 (1965).

Hauska, Von Günther et al., "Enzymatische Synthese Von [5-$^3$H] D–Fructose-1, 6-Biphosphat, [5-$^3$H] D–Glucose-6-Phosphat und [5-$^3$H] D–Glucose", 348 Hoppe-Seyler's Z. Physiol. Chem. 1273–1276 (1967).

Cohn, M. et al., "Nuclear Magnetic Resonance Assignment of the Vinyl Hydrogens of Phosphoenolpyruvate, Stereochemistry of the Enolase Reaction", 92 J. Am. Chem. Soc. 4095–4098 (1970).

Colowick, S. P. et al., (Eds), *Methods in Enzymology*, New York, Academic Press, 1955–Present, See: Serianni, A. S. et al., vol. 89 (1982), pp. 83–92, Mandl, I. et al., vol. 3 (1957), pp. 165–167, Korenberg, A., vol. 1 (1955), pp. 441–443.

Boyer, P. D. (Ed.), *The Enzymes*, 3rd Ed. New York, Academic Press, 1973, See: Nada, L., vol. 8, p. 302. Watts, D. C. vol. 8, pp. 428–429.

*Primary Examiner*—Howard E. Schain
*Attorney, Agent, or Firm*—Arnold, White & Durkee

[57] ABSTRACT

Utilizing the method of the present invention, a variety of aldose and ketose phosphates may be synthesized, labeled with $^{13}$C at any one of a number of single sites or synthetically related sites starting from $^{13}$C labeled pyruvate and using enzymes of the glycolytic pathway. The method of the present invention provides a quick and convenient method for the introduction of the $^{13}$C isotope into a variety of carbohydrates in a single step reaction. It also provides a method for the preparation of isotopically labeled carbohydrates in high yield, with little or no limitation on quantity, from commercially available labeled precursor.

10 Claims, 1 Drawing Figure

STEP 1

STEP 2

STEP 3

METHOD FOR ENZYMATIC SYNTHESIS OF ISOTOPICALLY LABELED CARBOHYDRATES

BACKGROUND OF THE INVENTION

The present invention relates to a method for the enzymatic synthesis of isotopically labeled aldose and ketose phosphates. More specifically, a method is provided for the synthesis of a number of aldose and ketose phosphates and their derivatives, labeled with $^{13}C$ at any one of a number of single sites or synthetically-related sites, starting from $^{13}C$-enriched pyruvate and using enzymes of the glycolytic pathway.

Present methods for the synthesis of labeled carbohydrates utilize a method involving the serial condensation of $^{13}C$-cyanide with an aldose to produce an aldose one carbon longer than the original aldose which is labeled at the reducing carbon. However, this method suffers from a number of disadvantages and limitations which decrease its utility. For example, to produce an aldose two carbons longer than the original aldose involves a lengthy purification step, via ion exchange and absorption chromatography, and a second condensation with cyanide to produce the longer aldose. Further, this method may be utilized for the labeling of only one or both of the two carbons at the reducing end of the molecule, and provides an overall yield of only 50–60%.

Methods are available for the enzymatic inter-conversion and condensation of isotopically labeled dihydroxyacetone phosphate and D-glyceraldehyde-3-phosphate to yield labeled D-fructose-1,6-diphosphate. The enzyme involved in this condensation, muscle aldolase, is also tolerant of accepting a wide variety of other 1–4 carbon aldehydes as substrates, making feasible the specific isotopic enrichment of a variety of 4–6 carbon ketose phosphates from isotopically-enriched dihydroxyacetone phosphate. Purified enzyme preparations are also available commercially for the conversion of the product ketose phosphate to phosphate analogs of D-glucose, D-mannose, D-galactose, D-ribulose and D-ribose, the latter via the pentose phosphate shunt, and other aldoses and ketoses.

At the other end of the glycolytic pathway, $^2H$ and $^{13}C$ enriched phospho(enol)pyruvate has been prepared in relatively high yield from isotopically labeled pyruvate using the enzyme phospho(enol)pyruvate synthetase. However, because of the large positive free energy change from pyruvate to dihydroxyacetone phosphate, via the enzyme catalyzed reaction of the glycolytic pathway, no method has been devised for the isotopic enrichment of aldose and ketose phosphates from labeled pyruvate.

SUMMARY OF THE INVENTION

Utilizing the method of the present invention, a variety of aldose and ketose phosphates may be synthesized, labeled with $^{13}C$ at any one of a number of single sites or synthetically related sites starting from $^{13}C$ labeled pyruvate and using enzymes of the glycolytic pathway. The method of the present invention provides a quick and convenient method for the introduction of the $^{13}C$ isotope into a variety of carbohydrates in a single step reaction. It also provides a method for the preparation of isotopically labeled carbohydrates in high yield, with little or no limitation on quantity, from commercially available labeled precursor. Further, the present invention provides a method of preparing isotopically labeled carbohydrates without lengthy, intervening chromatographic purification of intermediates, purification of the final product being the only chromatographic step, while retaining the option to recover isotopically labeled intermediates by chromatography or other means if so desired. The present invention also makes possible the preparation of isotopically labeled carbohydrates which, when incubated with the enzymes of various metabolic pathways, may be transformed into a variety of isotopically labeled reaction intermediates.

Carbohydrates labeled by this method may be used for the study of the structure and dynamic behavior of complex carbohydrates free in solution and existing as integral parts of glycoproteins, cell structural polysaccharides and other carbohydrate-containing molecules and cell structures. In addition, they may be used as spectroscopic substrate probes for studying lectins and other carbohydrate binding proteins. These labeled carbohydrates are particularly valuable as substrates or substrate precursors for the various enzymes involved in carbohydrate metabolism in biological systems and as tracers in biological systems.

DESCRIPTION OF THE INVENTION

The accompanying drawing, FIG. 1, is a schematic representation of a preferred embodiment of the present invention. The same process illustrated in FIG. 1 was used for the preparation of D-(3-$^{13}C$)-fructose-1,6-diphosphate from $^{13}C$-labeled pyruvate, as illustrated, and for other isotopically labeled carbohydrates from the appropriately labeled starting materials. The circled numbers are used to designate the labeled carbons of the three-carbon precursors and intermediates as referred to in the text. The primed numbers have been used to designate specific sites in the fructofuranose ring.

$^{13}C$-labeled ketose phosphates were prepared from $^{13}C$-labeled sodium pyruvate using the enzymes commonly found in the glycolytic and glyconeogenic pathways. In order to allow for the addition of reagents and the changes in pH needed to accommodate pH optima of some of the enzyme-catalyzed reactions, the synthetic scheme was carried out in three separate steps as summarized in FIG. 1 for D-(3-$^{13}C$)-fructose-1,6-diphosphate. However, a primary advantage of the present invention is the ability of the method to yield $^{13}C$-labeled aldose and ketose phosphates in a single reaction mixture. Stopping at intermediate steps was carried out only so as to provide a check on the yield of intermediates and to extract samples for nuclear magnetic resonance (NMR) analysis in order to verify the structure of the intermediates.

The first step of the reaction sequence involved the synthesis of phospho(enol)pyruvate (PEP) from $^{13}C$-labeled sodium pyruvate and adenosine triphosphate (ATP). Higher yields were obtained from this step using the glyconeogenic enzyme phospho(enol)pyruvate synthetase (PEPS) rather than the glycolytic enzyme pyruvate kinase. However, because of the highly unfavorable free energy charge associated with reverse glycolysis, this reaction generated a $^{13}C$-labeled PEP yield of approximately 50–60%. The reaction also gives adenosine monophosphate (AMP) and inorganic phosphate as products.

The reaction can be driven further towards completion by coupling it with the thermodynamically favorable breakdown of phosphocreatine to creatine involving the regeneration of ATP. To provide this coupled reaction, excess adenylate kinase was added to partially convert the AMP and ATP present in the reaction mixture to adenosine diphosphate (ADP) ($K_{eq}=1$). The addition of excess amounts of phosphocreatine and creatine phosphokinase resulted in phosphorylation of ADP to ATP ($K_{eq}=10^{10}$). Under the appropriate conditions, the coupling of these reactions in this manner allowed the conversion of essentially all the pyruvate to labeled PEP.

In the second step of the reaction, labeled PEP was incubated in the presence of excess yeast enolase, phosphoglycerate mutase and phosphoglycerate kinase. The product of this reaction, 1,3-diphosphoglycerate, is expected to be quickly hydrolyzed in aqueous solution to the more stable 3-phosphoglycerate (see Negelin, E., In: Colowick, S. P. and N. O. Kaplan (Eds.), *Methods in Enzymology*, vol. 3 (New York, Academic Press, 1957), pp. 216-220.).

In the third step of the reaction, $^{13}$C-labeled dihydroxyacetone phosphate (DHAP) is prepared from the step 2 reaction mixture by adding excess reduced nicotinamide adenine dinucleotide ($\beta$-NADH) and the enzyme glyceraldehyde phosphate dehydrogenase (GAPDH). Subsequent addition of muscle aldolase and an aldehyde to the $^{13}$C-labeled DHAP results in the production of the labeled 4-6 carbon ketose. The particular product formed depends on whether contaminating triose phosphate isomerase (TPI), which catalyzes the interconversion of DHAP to D-glyceraldehyde-3-phosphate, is removed (by denaturation with acid or otherwise) from the reaction mixture. Removal of TPI results in the formation of 4-6 carbon ketoses labeled at the carbon position corresponding to that at which the pyruvate was labeled. For instance, if the pyruvate starting material was labeled at 1-C and a three carbon long aldehyde is added, the six-carbon ketose formed will be enriched at the 3-C position.

If TPI is not removed, the resulting six-carbon ketose will be a mixture in which 50% will be labeled at 3-C and 50% will be labeled at 4-C. If 2-$^{13}$C sodium pyruvate is used, the result will be a 50—50 mixture of carbohydrates labeled at the 2-C and 5-C positions. If 3-$^{13}$C sodium pyruvate is used, the result will be 50—50 mixture of carbohydrates labeled at the 1-C and 6-C positions.

This entire reaction process may be carried out in one step, and in a typical reaction mixture, none of the original pyruvate could be detected by enzymatic assay using lactate dehydrogenase. In addition, the total amount of ketose phosphates prepared by this method was assayed to be within 10% of the amount of $^{13}$C-labeled pyruvate initially added.

The resulting labeled ketose may be used as the staring point for enzymatic conversion to other enriched carbohydrates. For instance, a six-carbon ketose may be converted, by known enzyme-catalyzed steps, to a six-carbon aldose or to a five-carbon aldose or ketose.

The invention may be better understood with reference to the following examples, in which the following materials, obtained from the following sources, were utilized. 1-$^{13}$C and 2-$^{13}$C sodium pyruvate (90% enrichment) were obtained from Merck & Co., Inc. (St. Louis, Mo.). PEPS (1.5 units/1 ml) was provided by Dr. William A. Bridger, Department of Biochemistry, University of Alberta, Canada. All other enzymes and cofactors, used without further purification, were obtained from Sigma Chemical Co. (St. Louis, Mo.).

EXAMPLE I 400 units of crystalline phosphocreatine kinase (130 units/mg), 50 units of adenylate kinase (25 $\mu$l, ammonium sulfate suspension) and 0.1 units of PEPS were added to a reaction mixture containing 10 mM 1-$^{13}$C sodium pyruvate, 20 mM ATP, 30 mM disodium phosphocreatine and 10 mM MgSO$_4$ in aqueous 0.2M Tris(-hydroxymethyl)aminomethane, pH 7.8 (12 ml total volume, 20% D$_2$O). This mixture was incubated at 25° C. for six hours, at which time, it was determined by $^{31}$P NMR and by an enzyme assay for pyruvate, involving its reduction by lactic dehydrogenase, that essentially all pyruvate had been enzymatically converted to PEP.

The pH of the mixture was adjusted to 6.65, and 150 units of crystalline yeast enolase (70 units/mg), 80 units of phosphoglycerate mutase (20 $\mu$l, ammonium sulfate suspension), and 60 units of phosphoglycerate kinase (20 $\mu$l, ammonium sulfate suspension) were added. The pH was adjusted with dilute HCl or dilute NaOH as necessary. After incubation for two hours at 25° C., it was ascertained by $^{31}$P NMR that better than 90% of the PEP had been converted to an equilibrium mixture of 3-phosphoglycerate and 1,3-diphosphoglycerate. Reduced $\beta$-NADH (to 0.13M) and 20 units of glyceraldehyde phosphate dehydrogenase (GAPDH) (10 $\mu$l, ammonium sulfate) were added. Within ten minutes of GAPDH addition, $^{31}$P NMR analysis indicated that essentially all the 3-phosphoglycerate had been converted to (1-$^{13}$C) DHAP.

The pH of the unfractional reaction mixture was then lowered to 2.0 with for one hour in order to remove contaminating triose phosphate isomerase (TPI) by protein denaturation. The pH was subsequently readjusted to 7.0 and a twofold molar excess of D-glyceraldehyde-3-phosphate and 2.0 units of rabbit muscle aldolase (100 $\mu$l, ammonium sulfate suspension) were added. After incubation for seven minutes, the pH was lowered to 4.0 and the presence of the product, D-(3-$^{13}$C)-fructose-1,6-diphosphate, was confirmed by $^{13}$C NMR.

To purify the D-(3-$^{13}$C)-fructose-1,6-diphosphate from the reaction mixture, the pH of the mixture was adjusted to 7.0 and the mixture applied to a 1.5$\times$20 cm column of DEAE-Sephadex$\pm$ (Pharmacia Fine Chemicals, Inc.), preequilibrated with 0.05M ammonium formate at pH 7.0. D-(3-$^{13}$C)-fructose-1,6-diphosphate was eluted from the column using a linear gradient of increasing buffer concentration (0.05 to 0.5M ammonium formate, 500 ml total volume). 10 ml fractions were collected at a flow rate of approximately 60 ml per hour. Alternate fractions were enzymatically assayed using the procedure set forth by I. Mandl and C. Neuberg, In: Colowick, S. P. and N. O. Kaplan (Eds.), *Methods in Enzymology*, vol. 3 (New York, Academic Press, 1957), pp. 165-167. To the pooled fractions was added an equivalent excess of washed Dowex$\pm$-50W (Dow Chemical Co.), hydrogen form, 200-400 mesh. The resin was filtered off, the product was evaporated to 2-3 ml under reduced pressure at 35° C. and the product was then lyophilized to dryness.

EXAMPLE II

D-(2,5-$^{13}$C)-fructose-1,6-diphosphate was prepared by essentially the same method as outlined in Example I with the following changes. (2-$^{13}$C) sodium pyruvate was used in place of (1-$^{13}$C) sodium pyruvate, TPI was not removed by denaturation, and no D-glyceraldehyde-3-phosphate was added.

EXAMPLE III

D-(3,4-$^{13}$C) fructose-1,6-diphosphate was prepared by essentially the same method as outlined in Example I with the following changes. TPI was not removed from the reaction mixture by denaturation and no D-glyceraldehyde-3-phosphate was added.

EXAMPLE IV

D-(3-$^{13}$C)-sorbose-1-phosphate was prepared by essentially the same method as outlined in Example 1 by adding an excess of L-glyceraldehyde-3-phosphate instead of adding D-glyceraldehyde-3-phosphate.

EXAMPLE V

D-(3$^{13}$C)-fructose-6-phosphate was prepared by essentially the same method as outlined in Example I by adding an excess of D-glyceraldehyde instead of adding D-glyceraldehyde-3-phosphate.

It should also be noted that D-(3-$^{13}$C)-fructose-6-phosphate could be prepared by preparing D-(3-$^{13}$C)-fructose-1,6-diphosphate in the manner outlined in Example I and incubating it with fructose-1,6-diphosphate phosphorylase, a commercially available enzyme, to produce D-(3-$^{13}$C)-fructose-6-phosphate.

EXAMPLE VI

D-(3-$^{13}$C)-xylulose-1-phosphate was prepared by essentially the same method as outlined in Example I by adding an excess of D-glycolaldehyde instead of adding D-glyceraldehyde-3-phosphate.

EXAMPLE VII

D-(3-$^{13}$C)-erythrulose-1-phosphate was prepared by essentially the same method as outlined in Example I by adding an excess of formaldehyde instead of adding D-glyceraldehyde-3-phosphate.

EXAMPLE VIII

D-(2-$^{13}$C)-fructose-1,6-diphosphate may be prepared by essentially the same method as outlined in Example I by using 2-$^{13}$C sodium pyruvate instead of 1-$^{13}$C sodium pyruvate.

EXAMPLE IX

D-(1-$^{13}$C)-sorbose-1-phosphate may be prepared by essentially the same method as outlined in Example IV by using 3-$^{13}$C sodium pyruvate instead of 1-$^{13}$C sodium pyruvate.

EXAMPLE X

D-fructose-1,6-diphosphate labeled at the 4-C, 5-C or 6-C positions may also be prepared by essentially the same method as outlined in Example I. For instance, D-(4-$^{13}$C)-fructose-1,6-diphosphate may be prepared by essentially the same method as outlined in Example I but with the addition of excess DHAP rather than D-glyceraldehyde phosphate. Likewise, to obtain D-(5-$^{13}$C)-fructose-1,6-diphosphate (or D-(6-$^{13}$C)-fructose-1,6-diphosphate), (2-$^{13}$C) sodium pyruvate (or (3-$^{13}$C) sodium pyruvate) is utilized as a starting material instead of (1-$^{13}$C)-sodium pyruvate and excess DHAP is added in place of D-glyceraldehyde phosphate.

EXAMPLE XI

D-(3-$^{13}$C)-5,6-dideoxy-arabino hexulose was prepared by essentially the same method as outlined in Example I by adding an excess of propionaldehyde instead of adding D-glyceraldehyde-3-phosphate.

EXAMPLE XII

The isotopically-labeled ketose phosphates prepared by the methods of Examples I–XI above, can also be used as the starting material for the enzymatic conversion of a particular ketose phosphate to an aldose, an aldose phosphate, or other carbohydrate or carbohydrate derivative. These conversions to other isotopically-labeled carbohydrate derivatives may be accomplished by incubation with enzymes of the various metabolic pathways as follows:

A. Preparation of Labeled 6-Phosphogluconate

A 2.7 ml solution was prepared which contained 2 mM D-(3-$^{13}$C) fructose-1,6-diphosphate, 2 mM EDTA, 10 mM NADP+, 20 mM MgSO$_4$ and 0.2M TRIS buffer. The pH was adjusted to pH 9.0 and 20 micro l of D-fructose-1,6-diphosphatase, (10 U/0.175 ml) 20 micro l of glucose-6-phosphate isomerase (200 U/mg protein) and 20 micro l of glucose-6-phosphate dehydrogenase (312 units/0.2 ml). 6-Phosphogluconate, labeled at the C-3 position, was isolated by standard chromatography methods.

B. Preparation of Labeled Glucose

Glucose labeled at any site may be prepared according to the present invention. For instance, D-(3-$^{13}$C)-fructose-1,6-diphosphate prepared according to Example I may be incubated with fructose-1,6- diphosphatase, phosphoglucoisomerase and glucose-6-phosphatase under the appropriate conditions to produce D-(3-$^{13}$C)-gluclose.

C. Preparation of Labeled Glucose Derivatives

A number of derivatives of glucose, labeled at any site may also be prepared. For instance, D-(3-$^{13}$C)-fructose-1,6-diphosphate prepared according to Example I may be incubated with fructose-1,6-diphosphate phosphatase, phosphoglucoisomerase and phosphoglucomutase under the appropriate conditions to produce D-(3-$^{13}$C)-glucose-1-phosphate. Further, D-(3-$^{13}$C)-glucose-1-phosphate may be converted to D-(3-$^{13}$C)-uridinediphosphate glucose, an important intermediate in the conversion of glucose to other hexoses and hexose derivatives, disaccharides, storage polysaccharides and the complex structural polysaccharides of cell walls, cell coats and intercellular spaces.

D. Preparation of Labeled Mannose Phosphates

D-(3-$^{13}$C)-fructose-1,6-diphosphate can also be used as the starting material to form other aldoses. For instance, it may be dephosphorylated by fructose-1,6-diphosphatase to D-(3-$^{13}$)-fructose-6-phosphate, which may then be incubated with phosphomannose isomerase to form D-(3-$^{13}$C)-mannose-6-phosphate.

E. Preparation of D-(2-$^{13}$C)-ribulose-5-phosphate and D-(2-$^{13}$C)-ribose-5-phosphate D-(2-$^{13}$C)-ribulose-5-phosphate and D-(2-$^{13}$)-ribose-5-phosphate were prepared as follows. 6-Phosphogluconate, enriched at the C-3 position, was prepared essentially as outlined in Example XI, A., above, but without the isolation of 6-phosphogluconate as a product. The pH of the reaction mixture was then lowered to 7.4, and 15 micro l of 6-phosphogluconate dehydrogenase (25 units/0.74 ml) was added. D-(2-$^{13}$C)-ribulose-5-phosphate was then isolated by standard chromatographic methods. Addition of 200 units of ribose-5-phosphate isomerase (200 units/mg protein) to the reaction mix before chromatographic purification of D-(2-$^{13}$C)-ribulose-5-phosphate resulted in the formation of D-(2-$^{13}$C)-ribose-5-phosphate, which was isolated by chromatography.

Ribose and ribulose phosphates labeled at the C-1 position may be prepared by starting with (2-$^{13}$C) sodium pyruvate instead of (1-$^{13}$C) pyruvate. All other steps are essentially the same as outlined above for the preparation of five carbon sugars labeled at the C-2 position.

F. Preparation of Labeled Amino Sugar

Isotopically-labeled fructose-1,6-diphosphate prepared by the method of Example I may also be used to make such carbohydrate derivatives as amino sugars. For instance, labeled fructose-1,6-diphosphate may be dephosphorylated to fructose-6-phosphate by incubation with fructose-1,6-diphosphatase. The labeled fructose-6-phosphate is then incubated with L-glutamine and hexose phosphate aminotransferase to form L-glutamate and 2-amino-2-deoxy-D-glucose-6-phosphate, labeled at the same carbon or carbons as the fructose diphosphate starting material.

G. Preparation of Labeled Sorbitol

Sorbitol labeled at any site may be prepared by the method of the present invention. For instance, D-(3-$^{13}$C)-fructose-1,6-diphosphate prepared according to Example I may be incubated with fructose-1,6-diphosphatase, phosphoglucoisomerase, glucose-6-phosphatase, glucose isomerase and sorbitol dehydrogenase under the appropriate conditions to produce D-(3-$^{13}$C)-sorbitol.

Using the methods of the above-disclosed examples, it will be seen by those skilled in the who have the benefit of this disclosure that a number of isotopically-labeled aldose and ketose phosphate and other carbohydrates or derivatives thereof may be made according to the method of the present invention, and that these carbohydrates may be labeled at any one of a number of single sites or synthetically-related sites. Further, it will be apparent that the isotopically labeled carbohydrates and carbohydrate derivatives could be prepared with pyruvate labeled with $^{14}$C or with $^{2}$H or $^{3}$H by the method of the present invention, and that pyruvate labeled at more than one site could be utilized to prepare aldose or ketose phosphates labeled at synthetically related sets of sites. Other variations will likely occur to those skilled in the art, all of which are considered to be part of the present invention, the scope of which is limited only by the scope of the following claims.

What is claimed is:

1. A method for preparing an isotopically labeled carbohydrate comprising:
   (a) incubating isotopically labeled pyruvate with a reaction mixture comprising adenosine triphosphate, phospho(enol)pyruvate synthetase, adenylate kinase, phosphocreatine, creatine kinase, enolase, phosphoglycerate mutase, phosphoglycerate kinase, B-NADH, glyceraldehyde phosphate dehydrogenase and aldolase to produce isotopically labeled carbohydrate said labeled pyruvate having an isotopic label at a position to result in the particular isotopically labeled carbohydrate being prepared and
   (b) isolating the isotopically labeled carbohydrate by chromatographic procedures.

2. The method of claim 1 wherein said isotopically labeled pyruvate is also incubated with dihydroxyacetone phosphate, an aldehyde or aldehyde derivative said aldehyde being one to three carbons long, and being selected according to the particular isotopically labeled carbohydrate being prepared.

3. The method of claim 2 wherein the reaction mixture is defined further as comprising contaminating triose phosphate isomerase activity which is removed therefrom.

4. A method for preparing an aldose, ketose, or derivative thereof isotopically labeled at one or more sites or synthetically related sets of sites comprising:
   (a) incubating isotopically labeled pyruvate with a reaction mixture comprising adenosine triphosphate, phospho(enol)pyruvate synthetase, phosphocreatine, creatine phosphokinase and adenylate kinase, said labeled pyruvate having an isotopic label at a position to result in the particular isotopically labeled aldose, ketose, or aldose or ketose derivative being prepared;
   (b) incubating the step (a) reaction mixture with enolase, phosphoglycerate mutase and phosphoglycerate kinase;
   (c) incubating the step (b) reaction mixture with B-NADH, glyceraldehyde phosphate dehydrogenase and aldolase; and
   (d) isolating the isotopically labeled aldose, ketose, or derivative thereof by chromatographic procedures.

5. The method of claim 4 wherein dihydroxyacetone phosphate, an aldehyde, or aldehyde derivative is added to the step (c) reaction mixture said aldehyde being one to three carbons long, and being selected according to the particular isotopically labeled aldose, ketose, or derivative thereof being prepared.

6. The method of claim 5 wherein the reaction mixture is defined further as comprising contaminating triose phosphate isomerase activity which is removed therefrom.

7. The method of claim 5 wherein said aldehyde, is a triose.

8. The method of claim 5 wherein dihydroxyacetone phosphate is added to the step (c) reaction mixture.

9. The method of claim 5 wherein an aldehyde or aldehyde derivative is added to the step (c) reaction mixture.

10. The method of claim 9 wherein said aldehyde or aldehyde derivative is formaldehyde, propionaldehyde, glyceraldehyde phosphate, glyceraldehyde or glycoaldehyde.

* * * * *